US00PP34491P2

(12) United States Plant Patent
Ullrich

(10) Patent No.: US PP34,491 P2
(45) Date of Patent: Aug. 16, 2022

(54) ROSE PLANT NAMED 'ESM R187'

(50) Latin Name: *Rosa hybrida*
Varietal Denomination: ESM R187

(71) Applicant: TECNOVIV LLC, Miami, FL (US)

(72) Inventor: Clarisse Ullrich, Quito (EC)

(73) Assignee: TECNOVIV LLC, Miami, FL (US)

( * ) Notice: Subject to any disclaimer, the term of this patent is extended or adjusted under 35 U.S.C. 154(b) by 0 days.

(21) Appl. No.: 17/669,084

(22) Filed: Feb. 10, 2022

(51) Int. Cl.
*A01H 5/02* (2018.01)
*A01H 6/74* (2018.01)

(52) U.S. Cl.
USPC ..... Plt./148

(58) Field of Classification Search
USPC ..... Plt./101, 141, 148
See application file for complete search history.

*Primary Examiner* — Karen M Redden
(74) *Attorney, Agent, or Firm* — C. Anne Whealy

(57) ABSTRACT

A new and distinct cultivar of Rose plant named 'ESM R187', characterized by its upright and strong flowering stems; vigorous growth habit; dark green-colored leaves; grown as a spray-type with numerous flowers per inflorescence; light pinkish yellow-colored flowers; and excellent postproduction longevity.

1 Drawing Sheet

Botanical designation: *Rosa hybrida.*
Cultivar denomination: 'ESM R187'.

STATEMENT REGARDING PRIOR DISCLOSURES BY INVENTOR and APPLICANT/ASSIGNEE

An European Community Plant Breeder's Rights application for the instant plant was filed by the Applicant/Assignee of the instant application, Tecnoviv LLC of Miami, Fla. on Mar. 9, 2019, application number 2019/0610. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'ESM R187'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in September, 2009 of a proprietary Rose selection identified as Line R376, not patented, as the female, or seed, parent with a proprietary Rose selection identified as Line R504, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in December, 2010.

Asexual reproduction of the new Rose plant by bud grafting in El Quinche, Pichincha, Ecuador since May, 2011 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM R187'. These characteristics in combination distinguish 'ESM R187' as a new and distinct Rose plant:

1. Upright and strong flowering stems.
2. Vigorous growth habit.
3. Dark green-colored leaves.
4. Typically grown as a spray-type with numerous flowers per inflorescence.
5. Light pinkish yellow-colored flowers.
6. Excellent postproduction longevity.

Plants of the new Rose differ from plants of the female parent selection in the following characteristics:

1. Plants of the new Rose are more vigorous and have longer stems than plants of the female parent selection.
2. Plants of the new Rose have larger leaves than plants of the female parent selection.

3. Plants of the new Rose have light pinkish yellow-colored flowers whereas plants of the female parent selection have orange-colored flowers.

Plants of the new Rose differ from plants of the male parent selection in the following characteristics:

1. Plants of the new Rose are more vigorous than plants of the male parent selection.
2. Leaves of plants of the new Rose have more serrated margins than leaves of plants of the male parent selection.
3. Plants of the new Rose have light pinkish yellow-colored flowers whereas plants of the male parent selection have yellow-colored flowers.
4. Flowering stems of plants of the new Rose have longer postproduction longevity than flowering stems of plants of the male patent selection.

Plants of the new Rose can also be compared to plants of *Rosa hybrida* 'SR 78200', not patented. In side-by-side comparisons, plants of the new Rose differ from plants of 'SR 78200' in the following characteristics:

1. Plants of the new Rose are taller than plants of 'SR 78200'.
2. Developing stems of plants of the new Rose have more anthocyanin than developing stems of plants of 'SR 78200'.

BRIEF DESCRIPTION OF THE PHOTOGRAPH

The accompanying colored photographic sheet illustrates the overall appearance of the new Rose plant showing the colors as true as it is reasonably possible to obtain in colored reproductions of this type. Colors in the photograph may differ slightly from the color values cited in the detailed botanical description which accurately describe the colors of the new Rose plant.

On the upper left of the photographic sheet is a side perspective view of a typical flowering stein of 'ESM R187'.

On the lower left of the photographic sheet is a close-up view of a typical flowering stein of 'ESM R187'.

At the upper right of the photographic sheet is a close-up view of a typical developed flower of 'ESM R187'.

And at the lower right of the photographic sheet are close-up views of the upper and lower surfaces of typical leaves of 'ESM R187'.

DETAILED BOTANICAL DESCRIPTION

The aforementioned photographs, following observations and measurements describe plants grown in ground beds in a polyethylene-covered greenhouse in Quito, Ecuador and under typical cut Rose production practices. Plants were pinched 14 weeks after planting and were five years old when the photographs and the description were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2015 Edition, except where general terms of ordinary dictionary significance are used.

Botanical classification: *Rosa hybrida* 'ESM R187'.

Parentage:

*Female, or seed, parent*.—Proprietary seedling selection of *Rosa hybrida* identified Line R376, not patented.

*Male, or pollen, parent*.—Proprietary seedling selection of *Rosa hybrida* identified Line R504, not patented.

Propagation:

*Type*.—By bud grafting.

*Time to initiate roots, summer*.—About 15 days at temperatures about 26° C. to 30° C.

*Time to produce a rooted young plant, summer*.—About 30 days at temperatures about 22° C. to 26° C.

*Root description*.—Medium in thickness, fibrous; typically greyish brown in color, actual color of the roots is dependent on substrate composition, water quality, fertilizers, substrate temperature and age of roots.

*Rooting habit*.—Moderately freely branching; dense.

Plant description:

*Plant and growth habit*.—Perennial shrub; upright and strong flowering stems; typically grown as a spray-type; vigorous growth habit and moderate growth rate.

*Productivity*.—Plants of the new Rose are highly productive with about 96.3 flowering stems developing per $m^2$ per year.

*Plant height*.—About 184.5 cm.

*Plant width* (*spread*).—About 61.5 cm.

*Lateral branches*.—Length: About 81.2 cm. Diameter: About 7.2 mm. Internode length: About 6.9 cm. Texture and luster: Smooth, glabrous; matte. Strength: Moderately strong to strong. Color, developing: Close to 146A and 177A. Color, developed: Close to 138A and NN137A. Thorns: Density: About one thorn per linear cm. Height: About 7.6 mm. Length, at base: About 9.4 mm. Color, immature: Close to 175A and 176A. Color, mature: Close to 174A.

Leaf description:

*Arrangement*.—Alternate; compound with typically three to seven leaflets per leaf.

*Leaf length*.—About 18.3 cm.

*Leaf width*.—About 15.3 cm.

*Leaflet length*.—About 7.7 cm.

*Leaflet width*.—About 4.7 cm.

*Leaflet shape*.—Oval.

*Leaflet apex*.—Acuminate.

*Leaflet base*: Obtuse.

*Leaflet margin*.—Serrate.

*Leaflet texture and luster, upper surface*.—Smooth, glabrous; semi-glossy.

*Leaflet texture and luster, lower surface*.—Smooth, glabrous; matte.

*Leaflet venation pattern*.—Pinnate.

*Leaflet color*.—Developing leaflets, upper surface: Close to NN137A and 187A. Developing leaflets, lower surface: Close to N199A. Fully expanded leaflets, upper surface: Close to 147A; venation, close to 144C. Fully expanded leaflets, lower surface: Close to 147B; venation, close to 144C.

*Petioles*.—Length: About 4.8 cm. Diameter: About 2.1 mm. Strength: Strong. Texture and luster, upper surface: Glandular, glabrous; matte. Texture and luster, lower surface: Smooth, glabrous; matte. Color, upper surface: Close to 143C. Color, lower surface: Close to 139D.

*Stipules*.—Arrangement and appearance: Two, adnate to the petiole, leafy in appearance. Length: About 2.9 cm. Width: About 2.1 mm. Shape: Roughly deltoid.

Apex: Acuminate, tapered. Base: Tapered. Margin: Variable. Texture and luster, upper and lower surfaces: Smooth, margins, pubescent; membranous; matte. Venation pattern: Pinnate.

Flower description:

*Flower type and arrangement*.—Symmetrical rosette flowers; flowers typically grown as spray-types with about four to seven flowers developing per inflorescence; flowers face upright.

*Flowering season*.—Plants of the new Rose flower year-round under greenhouse conditions; early flowering habit, plants begin flowering about 36 days after pinching.

*Spray height*.—About 25 cm.

*Spray diameter*.—About 17 cm.

*Flower diameter*.—About 2.4 cm.

*Flower depth* (*height*).—About 4.1 cm.

*Flower longevity*.—Excellent postproduction longevity; flowers maintain good substance for about 64 days on the plant and for about 14 to 16 days as a cut flower; flowers persistent.

*Fragrance*.—Moderately fragrant; pleasant.

*Flower buds*.—Length: About 4.4 cm. Diameter: About 2.6 cm. Shape: Ovoid. Texture and luster: Smooth, glabrous; slightly glossy. Color: Close to 144A and 146A.

*Petals*.—Quantity: About 44 to 49 per flower; petals imbricate. Length: About 3.1 cm. Width: About 2.7 cm. Shape: Nearly orbicular. Apex: Blunt to short acute. Base: Obtuse. Margin: Entire; undulate. Texture and luster, upper and lower surfaces: Rugose, glabrous; matte. Color: When opening, upper surface: Close to 20D; towards the base, close to 2D. When opening, lower surface: Close to 20D; towards the base, close to 4D. Fully opened, upper and lower surfaces: Close to 19D and 8C; venation, close to 19D and 8C; color becoming closer to 162A and 163A with subsequent development.

*Petaloids*.—Quantity: About five to ten in a single whorl; size and shape are variable. Texture and luster, upper and lower surfaces: Rugose, glabrous; matte. Color: When opening, upper and lower surfaces: Close to 20B and 4B. Fully opened, upper and lower surfaces: Close to 8C and 19B; venation, close to 8C and 19B; color becoming closer to 162D and 165B with subsequent development.

*Sepals*.—Quantity per flower: Typically five in a single whorl. Length: About 3.3 cm. Width: About 1.3 cm. Shape: Roughly deltoid. Apex: Tapered. Base: Truncate. Margin: Entire; ciliate. Texture and luster, upper and lower surfaces: Pubescent; matte. Color: When opening, upper surface: Close to 144A and 146A. When opening, lower surface: Close to 146D. Fully opened, upper surface: Close to 143B and 144B. Fully opened, lower surface: Close to 143A and 145C.

*Peduncles*.—Length: About 9 cm. Diameter: About 6 mm. Strength: Strong. Texture and luster: Smooth, glabrous; matte. Color: Close to 138A and NN137A.

*Reproductive organs*.—Stamens: Quantity: About 133 to 165 per flower. Filament length: About 7 mm. Filament color: Close to 3A to 3B. Anther size: About 2.6 mm by 2 mm. Anther shape: Reniform. Anther color: Close to 160A. Pollen amount: Moderate. Pollen color: Close to 21A. Pistils: Quantity: About 96 to 109 per flower. Pistil length: About 2.1 cm. Stigma diameter: About 1.4 mm. Stigma shape: Lobed. Stigma color: Close to 5D. Style length: About 1.4 cm. Style color: Close to 4C and 51A. Ovary color: Close to 144B to 144C. Receptacle height: About 1.3 cm. Receptacle diameter: About 1 cm. Receptacle shape: Cup-shaped. Receptacle texture: Smooth, glabrous. Receptacle color: Close to 144A to 144B. Fruits and seeds: To date, fruit and seed development have not been observed on plants of the new Rose.

Pathogen & pest tolerance: To date, plants of the new Rose have not been observed to be tolerant to pathogens and pests common to Rose plants.

Temperature tolerance: Plants of the new Rose have been observed to tolerate temperatures ranging from 9° C. to 23° C.

It is claimed:

1. A new and distinct Rose plant named 'ESM R187' as illustrated and described.

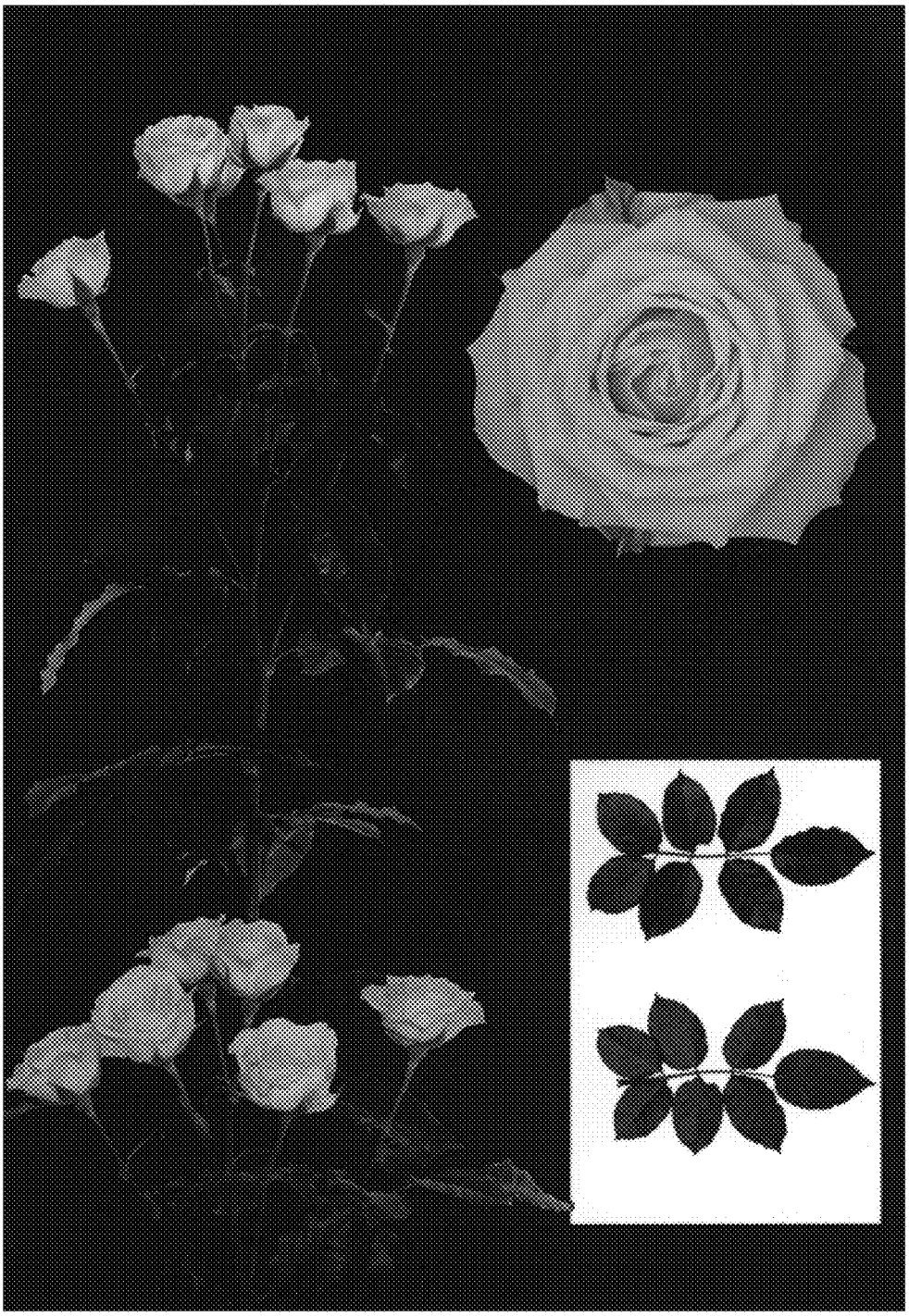

* * * * *